United States Patent [19]

Garrigus

[11] Patent Number: 4,837,795
[45] Date of Patent: Jun. 6, 1989

[54] TISSUE SPECIMEN HOLDING DEVICE AND BIOPSY PROCEDURE

[75] Inventor: George W. Garrigus, Dorsey, Ill.

[73] Assignee: Double D Double G Enterprises, Incorporated, St. Louis, Mo.

[21] Appl. No.: 78,091

[22] Filed: Jul. 27, 1987

[51] Int. Cl.⁴ ............................................. G03B 42/02
[52] U.S. Cl. .................................... 378/180; 378/177; 378/164; 378/37; 378/204
[58] Field of Search ........................... 378/37, 162–164, 378/177, 180, 204, 210, 480; 128/653, 659, 664

[56] References Cited

U.S. PATENT DOCUMENTS

| 1,904,234 | 4/1933 | Hoskin et al. | 378/164 |
|---|---|---|---|
| 2,344,823 | 3/1944 | Landis et al. | 378/164 |
| 2,539,323 | 1/1951 | Poittevin | 378/177 |
| 3,111,582 | 11/1963 | Levi | 378/164 |
| 4,122,350 | 10/1978 | Lipthay et al. | 378/180 |
| 4,259,585 | 3/1981 | Novak et al. | 378/37 |
| 4,563,768 | 1/1986 | Read et al. | 378/37 |
| 4,599,738 | 7/1986 | Panetta et al. | 378/37 |
| 4,649,275 | 3/1987 | Nelson et al. | 250/339 |
| 4,767,928 | 8/1988 | Nelson et al. | 250/339 |

FOREIGN PATENT DOCUMENTS 8701555  3/1987  PCT Int'l Appl. .................. 378/37

OTHER PUBLICATIONS

"Refinements in Diagnostic X-Ray Technics with the use of Wire Grids" by Fixott et al. in Jour. of the Amer. Dental Assoc., vol. 78, No. 1, Jan. 1969.
1-page article by K. I. Bickerstaff published in the British Journal of Surgery, vol. 71, No. 6, June. 1985.
Chapter 91 of "Radiology", vol. 1 by Daniel B. Kopans, 1986.

Primary Examiner—Craig E. Church
Assistant Examiner—John C. Freeman
Attorney, Agent, or Firm—Senniger, Powers, Leavitt and Roedel

[57] ABSTRACT

A device for holding a tissue specimen for radiographic exposure and assisting in the location of an abnormality in the specimen as detected by said radiographic exposure. The device comprises first and second platen members of radiolucent material, a radiopaque grid dividing one platen member into a plurality of regions, and a mechanism for drawing the two platen members toward one another thereby to compress a tissue specimen and flatten it to a substantially uniform thickness prior to radiographic exposure. An improved biopsy procedure utilizing the device is also disclosed.

12 Claims, 2 Drawing Sheets

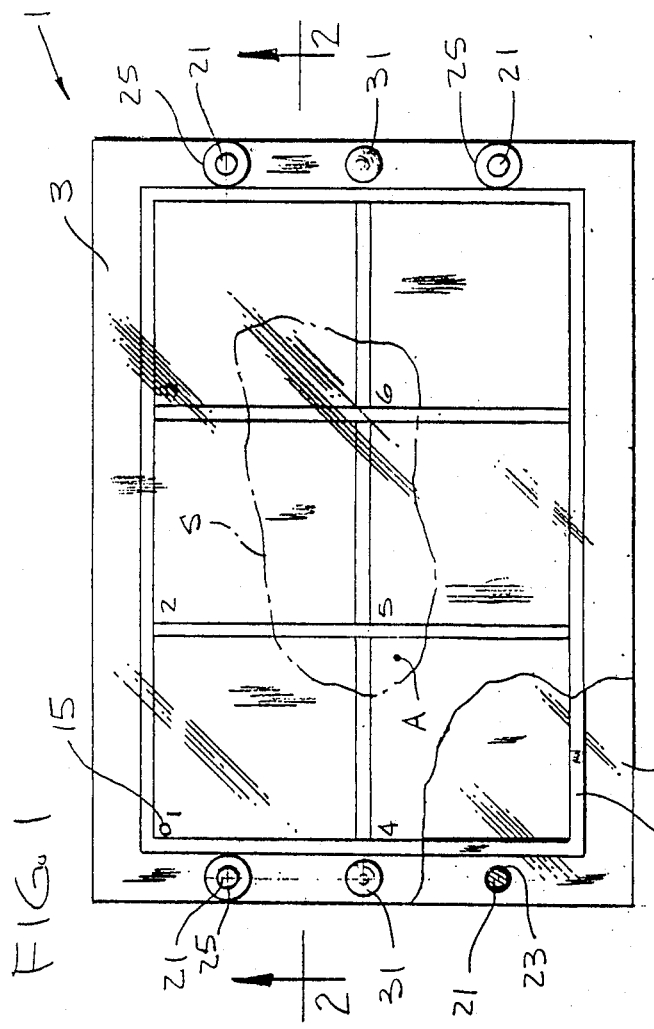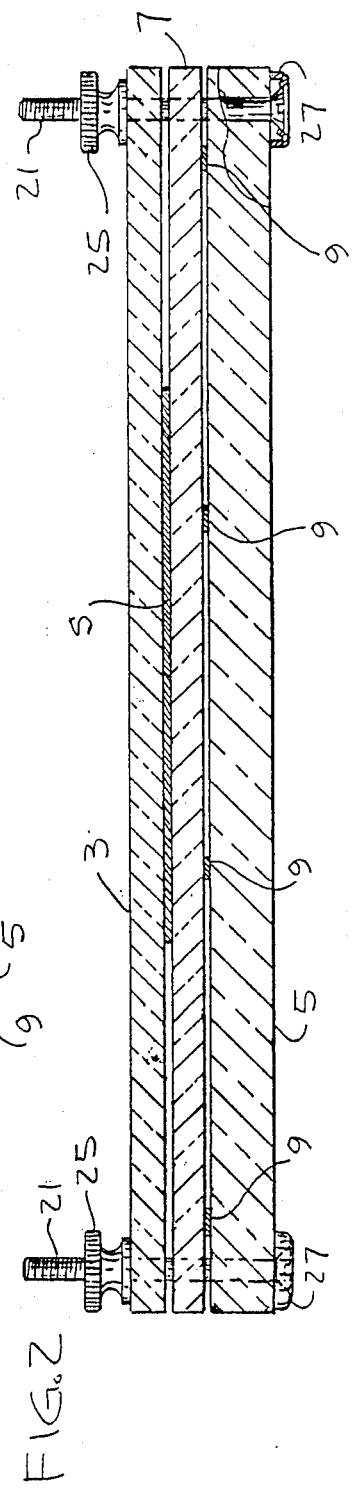

TISSUE SPECIMEN HOLDING DEVICE AND BIOPSY PROCEDURE

BACKGROUND OF THE INVENTION

This invention relates to a device adapted for holding a tissue specimen for radiographic exposure and subsequent pathological analysis, and to a biospy procedure utilizing such device.

The tissue holding device and biopsy procedure of the present invention have particular (but not exclusive) use in mammography, which is the radiographic study of the breasts, as for the detection of breast cancer. Conventional techniques for examination and treatment of the breasts involve radiographically exposing the breast using special mammographic equipment to determine if an abnormality (e.g., a microcalcification or lesion) is present in the breast, locating any such abnormality by inserting a needle-like pointer into the breast, surgically removing a specimen of the tissue in the area located by the pointer, and transporting the removed specimen to a pathologist for examination and analysis. Such examination and anlaysis takes place while the patient is still in surgery and typically involves freezing the specimen, slicing it into sections, and then microscopically examining the various frozen sections for the presence of the earlier detected abnormality. If the abnormality is located, it is examined and the results of the examination then conveyed to the surgeon for use in completing the surgery. If an abnormality is not located, another tissue specimen may have to be taken by the surgeon and the entire pathological process repeated.

It will be readily apparent, therefore, that to minimize the time a patient is being subjected to surgery, examination and analysis of the tissue specimen by the pathologist must be completed as expeditiously as possible. However, the conventional techniques described above are often less than expeditious. One reason for this is that the tissue specimen delivered to pathology may be relatively large and thus must be sliced into many sections, each of which must be separately analyzed. This process is both time-consuming and expensive. Moreover, in some instances, the specimen may not contain the abnormality, thereby necessitating the taking of another specimen for subsequent examination and analysis.

Accordingly, there is a need in the medical trade to expedite the process of analyzing a tissue specimen which may contain an abnormality, such as an abnormality indicative of breast cancer.

SUMMARY OF THE INVENTION

Among the several objects of this invention may be noted the provision of a device which is especially adapted for holding a tissue specimen during radiographic analysis and for relatively precisely locating an abnormality within the specimen, thereby reducing the time and expense incurred in examining and analyzing the specimen; the provision of such a device which is adapted for compressing the specimen to yield radiographs of higher resolution (i.e., showing greater detail); the provision of such a device which is adapted for use with mammographic radiographic equipment; the provision of such a device which is adapted for magnifying the abnormality as it is depicted on a radiograph for facilitating detection of the abnormality; the provision of such a device which is adapted for ready cleaning and sterilization; the provision of such a device which is simple in construction for economical manufacture; and the provision of an improved biopsy procedure which expedites the process of analyzing a tissue specimen which may contain an abnormality, such as an abnormality indicative of breast cancer.

Generally, a device of this invention is adapted for holding a tissue specimen for radiographic exposure and assisting in the location of an abnormality in the specimen as detected by the radiographic exposure. The device comprises first and second platen members of radiolucent material adapted to have a tissue specimen placed therebetween, radiopaque grid means dividing one platen member into a plurality of regions, means for drawing the two platen members toward one another thereby to compress the tissue specimen therebetween prior to radiographic exposure, and radiopaque orientation means associated with said grid means for orienting a radiograph having an image of said grid means and an image of said tissue specimen thereon to enable identification of the region or regions of said one platen member in which an abnormality is located.

The improved biopsy procedure of this invention comprises the following steps: radiographically exposing a part of the human body to detect the existence of any abnormality in that part of the body; applying locator means to the body generally to locate an abnormality detected by said radiographic exposure; surgically removing a specimen of tissue in the area located by said locator means; placing said specimen on radiopaque grid means divided into regions smaller than the specimen; radiographically exposing the specimen on said grid means to identify the region or regions in which the abnormality is located; separating the portions of specimen in the identified region or regions from the remainder of the specimen; and subjecting only the separated portions of specimen containing the abnormality to pathological analysis.

Other objects and features will be in part apparent and in part pointed out hereinafter.

BRIEF DESCRIPTION OF THE DRAWINGS

FIG. 1 is a plan view of a device of this invention for holding a specimen of tissue;

FIG. 2 is a cross sectional view along line 2—2 of FIG. 1;

Corresponding parts are indicated by corresponding reference numerals throughout the several views of the drawings.

DESCRIPTION OF THE PREFERRED EMBODIMENT

Figure 3:
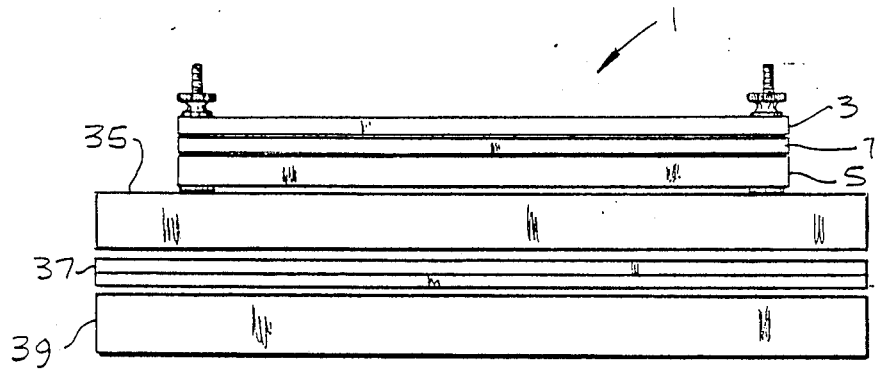
FIG. 3 is an elevational schematic illustrating the use of the device with mammographic equipment in the method of this invention.

Referring now to the drawings, there is generally indicated at 1 a device of this invention for holding a tissue specimen S for radiographic exposure of the specimen. As will appear, the device is especially adapted for assisting in the location of an abnormality (designated A in the drawings) in the specimen as detected by radiographic exposure. The device has particular (although not exclusive) application to breast tissue specimen examination, such as for breast cancer, which is a major cause of death among women, particularly between the ages of 45 and 50.

The device 1 comprises a first (upper) platen member and a second (lower) platen member in the form of two generally parallel plates designated 3 and 5, respectively, and an intermediate plate 7 disposed between the upper and lower platen members. All three plates 3, 5 and 7 are rectangular, have substantially the same overall width and length dimensions (e.g., ten inches by seven inches), and are of radiolucent substantially transparent material, such as a suitable acrylic plastic commercially available under the trademark "Plexiglas". The tissue specimen S is adapted to be placed between the upper platen member 3 and the intermediate plate 7 prior to radiographic exposure.

The lower platen member 5 has radiopaque grid means thereon comprising a grid 9 dividing the lower platen member into a plurality of regions (e.g., six regions). Because the grid is to assist in the location of any abnormality A in the tissue specimen S, the regions should be sized so that each is substantially smaller than the tissue specimen. The grid is formed by lines of radiopaque material, such as stripes of radiopaque paint or strips of radiopaque tape, so that the lines are visible on any radiograph taken of the specimen S held by the device 1. Each region of the grid is preferably suitably identified, as by reference numerals (e.g., numerals 1–6 in FIG. 1). A small radiopaque ball 15 is also embedded in the lower platen member at one corner of the grid 9 (the upper lefthand corner as viewed in FIG. 1). The radiopaque region designations and the ball 15 constitute means for orienting a radiograph having an image of the grid 9 and an image of the tissue specimen S thereon to enable identification of the region or regions of the lower platen member in which an abnormality A is located, as will be explained hereinbelow.

A plurality of plastic screws, each designated 21, extend up through holes 23 in the three plates 3, 5, 7, and nuts indicated at 25 are threaded on the threaded shank of the screws 21. Thus, by tightening the nuts on the screws, the upper and lower platen members may be drawn toward one another to compress the tissue specimen S therebetween prior to radiographic exposure to squeeze excess fluids from the specimen and to flatten it to have substantially the same overall thickness and density. This results in a radiographic image of higher-resolution (sharper detail) and facilitates detection of any abnormality in the specimen. The screws 21 are suitably spaced around the plates to provide for relatively uniform compression of the specimen, four such screws being depicted in the drawings. The heads of the screws are received in annular standoffs 27 on the underside of the lower platen member 5. The standoffs function as legs for the device. The screws are secured (as by glue) in the holes 23 through the lower platen member to prevent unintentional separation of the screws from the lower platen member. The screws extend freely up through the screw holes 23 in the intermediate plate 7 and upper platen member 3 to permit ready separation of the latter two plates from the lower platen member 5.

To position the tissue specimen S in the device 1, the nuts 25 are removed from the screws 21 and the upper platen member 3 lifted via handles 31 at opposite sides of the member away from the intermediate plate. The tissue specimen is then placed on the intermediate plate 7, the upper platen member lowered into position, and the nuts 25 tightened on the screws to compress the tissue specimen to prepare it for radiographic exposure.

Figure 4:
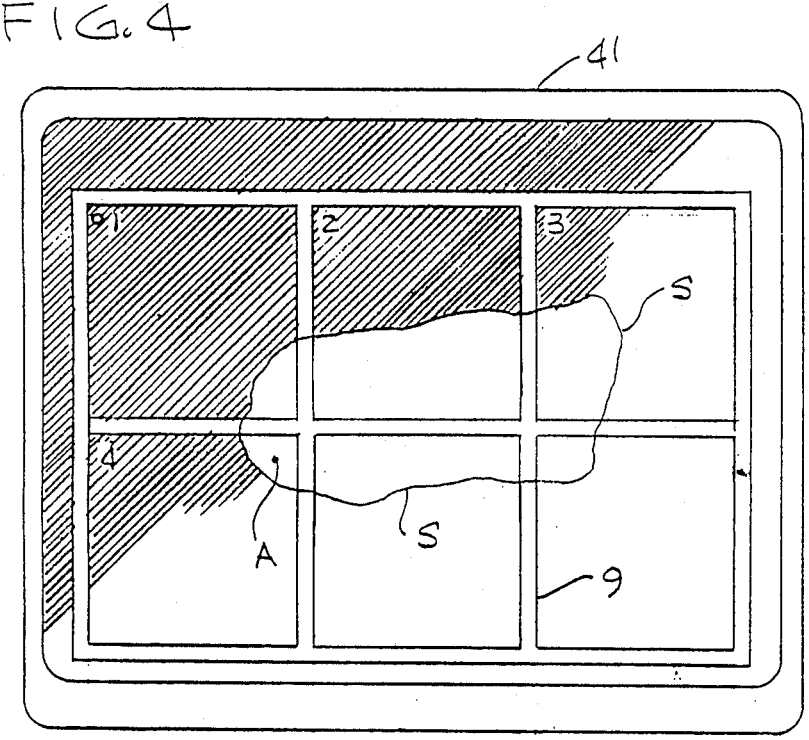
FIG. 4 is a radiograph of a specimen (e.g., breast tissue) held by the device of this invention.

One of the important advantages of the device 1 of this invention is that it is adapted for use in conjunction with mammographic equipment, such as a mammographic unit of the type sold by Thomson CGR Medical Corporation under the model designation CGR 500T. The use of the device with this type of unit is shown schematically in FIG. 3, where the holder is shown placed on a breast support surface 35 of the unit. X-ray film 37 is positioned immediately below surface 35 and a phototiming device 39 is disposed below the film for measuring the amount of radiation passing through the film. After appropriate exposure of the film, the phototiming device is adapted to stop further exposure, thereby ensuring a high-quality radiograph to facilitate detection of an abnormality A in the tissue specimen S. FIG. 4 shows such a mammogram 41, the radiographic images being identified by reference numerals or characters corresponding to the objects they represent. It has been discovered that the device 1 of the present invention aids in providing a high-quality radiograph by attenuating the X-ray beam to an extent necessary to provide a relatively clear, high-resolution image. The plates 3, 5 and 7 should be a sufficient thickness and density to accomplish this. Excellent results have been obtained by using plates 3, 5 and 7 of acrylic plastic (such as is sold under the trademark "Plexiglas") having thicknesses of 0.25 in., 0.50 in. and 0.25 in., respectively.

A further advantage of using the device of the present invention is that the tissue specimen S is spaced a greater distance above the X-ray film than in conventional X-ray techniques, such as the well-known tabletop technique where the specimen is placed directly on a conventional radiographic cassette. The fact that tissue specimen is spaced further away from the film is believed to magnify the image of any abnormality in the specimen to facilitate detection and examination.

The device 1 is especially adapted for use in the improved biopsy procedure of the present invention. This procedure or method involves the steps described below.

A part of the human body is radiographically exposed at a first location (e.g., a radiology room in a hospital) to detect the existence of any abnormality in that part of the body. In a situation involving mammography, the human body part in question is a female breast, and the radiographic exposure is typically by mammographic equipment of the type discussed above. This involves placing the breast on a support surface (e.g., suface 35), compressing it by means of a compression plate, and then exposing the breast to low-enery radiation to obtain a mammogram. Two mammograms are typically taken, one with the breast in a craniocaudad position and another with the breast in a mediolateral position. The mammograms are then examined by a radiologist to detect the presence of any abnormality (e.g., a minute calcification or lesion) that might be indicative of breast cancer.

Assuming that an abnormality A is detected, it is then located by applying locator means to the patient. This may be accomplished by inserting a needle-like pointer into the breast generally in the area of the abnormality as detected by the mammogram(s). The patient is then transported to surgery where a specimen of breast tissue in the area located by the aforesaid pointer is surgically removed.

After the tissue specimen has been removed, but prior to completion of the surgery, the specimen is transported back to radiology where it is placed in the holding device 1 of this invention as described earlier. The device should be properly cleaned prior to placement of the specimen therein, as by using a solution of 70% isopropyl alchohol. It is also preferable that a preliminary exposure of the device be made at some time prior to its use to ensure that no artifacts are present in the plates 3, 5 and 7 which might be mistaken for an abnormality in the tissue specimen to be examined.

The device 1 holding the tissue specimen S is placed on surface 35 of the same mammographic unit used in step 1 and radiographically exposed to low-energy X-rays (preferably not in excess of 28 KVP) to obtain a radiograph having an image of the specimen S against the background of the grid 9 (see FIG. 4). The radiograph is then examined for the presence of the abnormality. If no abnormality is found, the surgeon is advised so that he can take appropriate action, which may involve surgically removing another tissue specimen for further radiographic analysis. If an abnormality is shown on the radiograph, the radiograph and the device 1 (still holding the specimen) is transported to a different location for pathological analysis (e.g., a pathology room of the same hospital). During this transport it is important that the specimen remains in fixed position with respect to the grid 9.

Once in pathology, a pathologist inspects the radiograph and uses the metal ball 15 and/or reference designations (e.g., 1-6) as depicted on the radiograph to identify the region or regions of the lower platen member 5 in which the abnormality is found. Referring to FIG. 4, for example, the abnormality would be identified as being in region 4. He then removes the upper platen member 3 from the device 1 (being careful not to disturb the position of the specimen relative to the grid 9) and isolates the portion of the tissue specimen in the region or regions containing the abnormality. This is accomplished by separating (e.g., cutting) the stated portion of the tissue specimen from the remainder of the specimen. This portion is then subjected to pathological analysis, which typically involves freezing the tissue, slicing it into sections and microscopically examining each section until the abnormality is found and analyzed.

Finally, the pathologist's report is transmitted to the surgeon for appropriate action.

It will be apparent, therefore, that by pinpointing the portion of the tissue specimen containing the abnormality, the time and expense involved in effecting the pathological analysis of the tissue specimen containing the abnormality is reduced considerably as compared to the conventional process where the pathologist is required to freeze, slice and examine the entire tissue specimen, which can take an extended period of time. The time savings resulting from this invention important not only from the standpoint of the pathologist, but the surgeon and the patient as well, since the duration of surgery is also minimized. Moreover, since the same mammographic unit is used throughout the procedure, the quality and consistency of the mammograms and the specimen radiographs are maximized to facilitate detection of any abnormality.

In view of the above, it will be seen that the several objects of the invention are achieved and other advantageous results attained.

As various changes could be made in the above constructions and method without departing from the scope of the invention, it is intended that all matter contained in the above description or shown in the accompanying drawings shall be interpreted as illustrative and not in a limiting sense.

What is claimed is:

1. A portable device for use in conjunction with an X-ray machine but structurally independent of said X-ray machine, said portable device having means for holding a surgically removed tissue specimen during radiographic exposure of the specimen by said X-ray machine and for assisting in the subsequent isolation of an abnormality in the specimen as detected by said radiographic exposure, said portable device comprising first and second platen members of radiolucent material, radiopaque grid means dividing one platen member into a plurality of regions, means for drawing the two platen members toward one another for compressing a tissue specimen between the platen members and flattening the specimen to a substantially uniform thickness prior to radiographic exposure by said X-ray machine, said means for drawing the two platen members toward one another comprising a plurality of screws extending through holes spaced around the periphery of the platen members, and nuts threadable on the screws, and radiopaque orientation means associated with said grid means for orienting a radiograph having an image of said grid means and an image of said tissue specimen thereon to enable identification of a region or regions of said one platen member in which an abnormality is located, said device being sufficiently small to enable it to be hand carried by a single person from one location where a tissue specimen held by said portable device is subjected to radiographic exposure by said X-ray machine to another location remote from said X-ray machine where any abnormality in said specimen may be isolated and analyzed.

2. A device as set forth in claim 1 wherein said first and second platen members comprise a pair of generally parallel plates of substantially transparent material.

3. A device as set forth in claim 2 wherein said radiopaque grid means comprises a grid formed by lines on said second platen member.

4. A device as set forth in claim 3 wherein said grid lines are formed by strips of radiopaque tape adhered to one face of the second platen member.

5. A device as set forth in claim 3 further comprising an intermediate plate of radiolucent substantially transparent material disposed between said first and second platens and generally parallel thereto.

6. A device as set forth in claim 1 further comprising handle means on said first platen member to facilitate separation of the platen members to permit placement of a tissue specimen therebetween.

7. A device as set forth in claim 1 wherein said first and second platen members have a thickness and density sufficient to produce a relatively clear radiographic image of said tissue specimen using mammographic radiograph equipment.

8. A device as set forth in claim 7 wherein said first and second platen members have a combined thickness of at least about 0.75 inches.

9. A device as set forth in claim 8 wherein said first and second platen members are of substantially transparent acrylic plastic.

10. A device as set forth in claim 8 further comprising an intermediate plate of radiolucent substantially transparent material disposed between said first and second platens and generally parallel thereto.

11. A device as set forth in claim 10 wherein said intermediate plate is approximately 0.25 inches thick.

12. A portable device for use in conjunction with X-ray film in a container, said portable device having means for holding a surgically removed tissue specimen during radiographic exposure of the specimen and for assisting in the subsequent isolation of an abnormality in the specimen as detected by said radiographic exposure, said portable device comprising a substantially solid upper platen member, a substantially solid lower platen member, and a substantially solid intermediate platen member between the upper and lower platen members, each of the upper, lower and, intermediate platen members being of radiolucent material to enable passage of X-rays through all three plates to said X-ray film positioned therebelow, said upper, lower and intermediate platen members being structurally independent of said X-ray film and said container, radiopaque grid means dividing one platen member into a plurality of regions, means for drawing at least two of the platen members toward one another for compressing a tissue specimen between said two platen members and flattening the specimen, including an area of the specimen containing said abnormality, to a substantially uniform thickness prior to radiographic exposure, and radiopaque orientation means associated with said grid means for orienting a radiograph having an image of said grid means and an image of said tissue specimen thereon to enable identification of the region or regions of said one platen member in which an abnormality is located, said portable device being sufficiently small to enable it to be readily carried by a single person form one location where a tissue specimen held by said portable device is subjected to radiographic exposure to another location where any abnormality in said specimen may be isolated and analyzed.

* * * * *